United States Patent [19]

Lafon

[11] Patent Number: 4,758,560

[45] Date of Patent: Jul. 19, 1988

[54] PHENYL-(3-HEXAMETHYLENEIMINO-PROPYL)-KETONE

[75] Inventor: Louis Lafon, Paris, France

[73] Assignee: Societe Anonyme Dite: Laboratoire L. Lafon, Maisons Alfort, France

[21] Appl. No.: 883,265

[22] Filed: Jul. 8, 1986

[30] Foreign Application Priority Data

Jul. 10, 1985 [FR] France ................................ 85 10551

[51] Int. Cl.⁴ ...................... A61K 31/55; C07D 223/04
[52] U.S. Cl. ....................................... 514/212; 540/610
[58] Field of Search ........................... 540/610; 514/212

[56] References Cited

U.S. PATENT DOCUMENTS 3,895,030  7/1975  Lafon ............................... 540/610 X
4,465,678  8/1984  Knops et al. ...................... 540/610 X

FOREIGN PATENT DOCUMENTS 2534916  4/1984  France ............................. 540/610 X

OTHER PUBLICATIONS

Kudrin et al., Chem. Abstracts, 68 (1968), entry 94451b.
Profft et al., Chem. Abstracts, 68, (1968), entry 95658m.
Mar., Ed., *Advanced Organic Chemistry* 2nd ed. (1977) pp. 847–848.

*Primary Examiner*—Donald G. Daus
*Assistant Examiner*—William A. Teoli, Jr.
*Attorney, Agent, or Firm*—Kuhn and Muller

[57] ABSTRACT

The present invention relates to phenylalkylaminoketone derivatives, namely the phenyl-(3-hexamethyleneiminopropyl)-ketone and its addition salts, by way of new industrial products.

These new products are useful in therapy as vasodilating agents.

4 Claims, No Drawings

PHENYL-(3-HEXAMETHYLENEIMINOPROPYL)-KETONE

FIELD OF THE INVENTION

This invention relates, by way of new industrial products, to phenyl-(3-aminopropyl)-ketone derivatives, namely the phenyl-(3-hexamethyleneiminopropyl)-ketone and its addition salts. It also relates to the method of preparation and the use in therapy of these new compounds, especially as cardiovascular agents in view of their profitable vasodilating properties.

PRIOR ART

It is known that a number of (phenyl)-(aminoalkyl)-ketone derivatives have already been described in which the phenyl ring is substituted by alkoxy and/or hydroxy groups, see in particular FR-A-1 492 256, FR-A-5636M, FR-A-2 404 003, FR-A-2 534 916, GB-A-1 078 975, GB-A-1 115 992, U.S. Pat. No. 3,895,030 and A. BOUCHERLE et al., Chimie Thérapeutique 3 (No. 4), 256–259, (1968), wherein said derivatives are presented as anti-inflammatory agents, analgesics, antipyretic agents, antispasmodic agents, tranquilizers, vasodilating agents and/or bradycardia inducing agents.

It is known, in particular from FR-A-2 404 003, that there is no structure-activity relationship amongst the phenyl-(aminoalkyl)-ketone family, the pharmacological effects being modified or disappearing in function of the nature of the substituents on the phenyl ring, of the nature of the amino group, and at last of the nature of the aliphatic hydrocarbon group being present between the CO group and the amino group.

DETAILED DISCLOSURE OF THE INVENTION

It has just been found that the compounds according to this invention, which are structurally different from the previously disclosed or suggested compounds, are particularly interesting as pharmaceuticals in view of their improved vasodilating properties and their lower toxicity by comparison with their nearest known analogues.

Results of comparative assays given in table I hereinafter point out that, with respect to (a) (2,4,6-trimethoxyphenyl)-(3-pyrrolidinopropyl)-ketone hydrochloride (Code No: LL 1656), which is disclosed in U.S. Pat. No. 3,895,030 and commercialized under the trademark "Fonzylane" (international nonproprietary name: "buflomedil hydrochloride") and which is a reference vasodilating agent, and (b) (2,4,6-trimethoxyphenyl)-(3-hexamethyleneiminopropyl)-ketone hydrochloride (Code No.: CRL 41 080), which is disclosed in FR-A-2 534 916, phenyl-3-hexamethyleneiminopropyl)-ketone hydrochloride (Code No.: CRL 41 339) according to this invention is more active as a vasodilating substance per introduodenal route, and, less toxic.

The new phenyl-aminoalkyl-ketone derivatives according to this invention are characterized in that they are selected from the group comprising (a) the phenyl-(3-hexamethyleneimiopropyl)-ketone of the formula

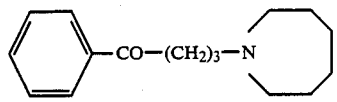

and, (b) its addition salts,

The expression "addition salts" is understood here as meaning firstly the acid addition salts obtained by reacting the free base of the formula I with inorganic or organic acids, and secondly the ammonium salts.

Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the base of the formula I. $CH_3I$ and $CH_3Cl$ may be mentioned in particular among the compounds making it possible to obtain ammonium salts. In general terms, the acid addition salts are preferred to the ammonium salts.

The base of the formula I can be prepared in accordance with a method known per se, by application of classical reaction mechanisms. The method recommended here consists in reacting 4-hexamethyleneimino-butyronitrile with phenylmagnesium bromide for at least 1 hour at a temperature between 0° and 25° C., in a suitable anydrous solvent, using advantageously more than 1 mol (preferably 2 mols) of $C_6H_5MgBr$ per 1 mol of 4-hexamethyleneimino-butyronitrile. Amongst the solvents, which are suitable here, can be cited in particular ethers such as dimethyl ether, diethyl ether, tetrahydrofuran and mixtures thereof.

Phenyl-(3-hexamethyleneiminopropyl)-ketone and its addition salts are useful agents in the treatment of diseases of the cardiovascular system; they act as peripheral vasodilating agents and bradycardia inducing agents.

According to the invention, a therapeutical composition is provided which comprises, in association with a physiologically acceptable excipient, at least a compound selected rom the group comprising the phenyl-(3-hexamethyleneiminopropyl)-ketone, its non-toxic addition salts and mixtures thereof, as the active ingredient.

Of course, in a composition of this type, the active ingredient is present in a pharmaceutically effective amount.

It is further recommended in accordance with this invention to use a substance selected from the group comprising the phenyl-(3-hexamethyleneiminopropyl)-ketone and its non-toxic addition salts, for obtaining a vasodilating medicament intended for a therapeutical use to patients suffering from circulatory disorders of lower limbs) and in need of such a medicament.

Further advantages and characteristics of the invention will be understood more clearly on reading the following description of a preparative example and the results of pharmacological assays; these elements as a whole do not imply a limitation but are given by way of illustration.

PREPARATION

Preparation of phenyl-(3-hexamethyleneiminopropyl)-ketone hydrochloride (Example 1; Code No.: CRL 41 339).

Other nomenclatures: 1-benzoyl-3-hexamethyleneimino-propane hydrochloride, or (4-hexamethyleneimino-1-butyryl)-benzene hydrochloride.

In a 88 ml (0.2650 mol) solution of phenylmagnesium bromide 3M in diethyl ether kept at 0° C., is poured in 1 hour a solution of 22 g (0.1325 mol) of 4-hexamethyleneimino-butyronitrile in 50 ml of diethyl ether. The reaction mixture is left overnight at room temperature (15°–20° C.) then poured onto a mixture of iced water (220 ml) and HCl 12N (110 ml). After stirring for 1 hour, the precipitate, which is formed is isolated by filtration then suspended in water. After alkalinization with concentrated NaOH and extraction with diethyl ether, 26 g of a lightly yellow oil are obtained. This oil is treated, in diethyl ether, with HCl-containing ethanol to give a precipitate which is recovered. By recrystallization from anhydrous ethanol 25,8 g (yield: 69.2%) of CRL 41 339 are obtained as a white powder which is very soluble in water (100 g/l).

$MP_{inst} = 192°$ C.

The results of the assays which were undertaken with the CRL 41 339 have been summarized below.

I. TOXICITY

In mice, per intraperitoneal route, the LD-0 (maximum non-lethal dose) in mice is higher than 64 mg/kg, the LD-30 (lethal dose for 30% of the treated animals) is of about 128 mg/kg, and the LD-100 (minimum lethal dose for all the treated animals) is lower than or equal to 256 mg/kg.

II. CARDIOVASCULAR STUDY

The study of the cardiovascular properties has been performed on nembutal-anesthetized dogs, CRL 41 339 being administered intra-duodenally in solution in physiological saline (bidistilled water containing 9 g/l of NaCl) at pH 7.5 (the maximum concentration of CRL 41 339 used being of 32.4 mg/ml).

Three dogs (average weight: 14.3 kg), anesthetized with nembutal, receive CRL 41 339 by intraduodenal administration at successive doses of 0.1 mg/kg, 0.5 mg/kg, 1 mg/kg, 2.5 mg/kg, 5 mg/kg and 10 mg/kg, then two of these dogs receive a supplemental dose of CRL 41 339 (10 mg/kg) by intravenous administration.

The arterial blood pressure, the heart rate, the blood flow through the femoral artery, the blood flow through the vertebral artery and the rectal and cutaneous temperatures are measured.

It is found that CRL 41 339 administered per I.D. route highly increases (as from the dose of 2.5 mg/kg—i.e. at the accumulated dose of 4.1 mg/kg) the femoral artery flow, that it does not modify the blood arterial pressure and the heart beat, and that it reduces the respiration rate.

The supplemental dose of 10 mg/kg I.V. of CRL 41 339 induces hypotension and bradycardia.

The effects of isoprenaline, tested after an accumulated dose of 19.1 mg/kg of CRL 41 339, administered intraduodenally, are slightly reduced as regards the heart rate, and are not modified as regards the diastolic blood pressure:

with 1 μg/kg of isoprenaline, the diastolic blood pressure changes from 117 mm Hg (i.e. about $1.5 \times 10^4$ Pa) to 37 mm Hg (i.e. about $4.9 \times 10^3$ Pa) after CRL 41 339, instead of changing from 144 mm Hg (i.e. about $1.9 \times 10^4$ Pa) to 36 mm Hg (i.e. about $4.8 \times 10^3$ Pa) in the control animals (i.e. anesthetized dogs receiving only isoprenaline), and the heart rate changes from 175 beats/minute to 238 beats/minute after CRL 41 339, while in the control animals said heart rate increases from 188 beats/minute to 253 beats/minute.

It is also observed that the noradrenaline-induced hypertension is reduced by CRL 41 339 (at an accumulated dose of 19.1 mg/kg I.D.):

with 2 μg/kg of noradrenaline the systolic blood pressure increases from 160 mm Hg (i.e. about $2.1 \times 10^4$ Pa) to 253 mm Hg (i.e. about $3.3 \times 10^4$ Pa) after administration of CRL 41 339 at an accumulated dose of 19.1 mg/kg I.D., while in the control animals, (anesthetized dogs receiving only noradrenaline) the blood systolic pressure increases from 181 mm Hg (i.e. about $2.4 \times 10^4$ Pa) to 301 mm Hg (i.e. about $4 \times 10^4$ Pa).

III. COMPARATIVE ASSAYS

CRL 41 339 according to this invention has been compared to analogous compounds (i.e. reference compound A-1, and compound A-3) and to a homologous compound (compound A-2). The results given in table I hereinafter point out the superiority of CRL 41 339 (Ex I) vis-a-vis the previously known structurally close products, as regards toxicity and peripheral vasodilating activity.

IV. CLINICAL ASSAYS

In clinical trials, good results were obtained on adult human beings after administration of CRL 41 339 as vasodilating agent, in particular in the treatment of (i) arteritis manifestations in lower limbs, and (ii) ulcers of arterial or venous origin in lower limbs.

The posology which is recommended consists in administering to man tablets or gelatine capsules each containing 100 mg of CRL 41 339, at a rate of 2 to 3 tablets or gelatine capsules per day.

TABLE I $AR-CO-(CH_2)_3-B$, HCl

| Product | Code N° | Ar | B | LD-50 I.V. mice (mg/kg) | MVD (e) (mg/kg) | therapeutical index (h) |
|---|---|---|---|---|---|---|
| Ex 1 (a) | CRL 41 339 | $C_6H_5$ | hexamethyleneimino | 128 (f) | 4.1 | 0.032 |
| A-1 (b) (c) | LL 1656 | 2,4,6-$(OCH_3)_3C_6H_2$ | pyrrolidino | 60 | 6 | 0.100 |
| A-2 (d) | CRL 41 080 | 2,4,6-$(OCH_3)_3C_6H_2$ | hexamethyleneimino | 96 | 5 | 0.053 |

TABLE I-continued

| | | AR—CO—(CH₂)₃—B, HCl | | | | |
|---|---|---|---|---|---|---|
| Product | Code N° | Ar | B | LD-50 I.V. mice (mg/kg) | MVD (e) (mg/kg) | therapeutical index (h) |
| A-3 (c) | LL 1647 | 2,4,6-(OCH₃)₃C₆H₂ | piperidino | 68 | (g) | 0 |

Notes
(a) product according to the invention;
(b) reference vasodilating agent;
(c) disclosed in US-A- 3 895 030;
(d) disclosed in FR-A- 2 534 916;
(e) minimum dose inducing in nembutal-anesthetized dogs a femoral vasodilating action (tested products being administered per I.D. route).
(f) 128 mg/kg is approximately the LD-50 I.V. of CRL 41 339;
(g) no vasodilating action per I.D. route;
(h) MVD/LD-50 ratio

V. SUPPLEMENTARY ASSAYS

Results of supplementary assays carried out with CRL 41 339 are summarized hereinafter.

(a) Mutagenic activity.

It is found that CRL 41 339 is devoid of mutagenic activity, in particular on *Salmonella typhimurium*.

(b) Action on rabbit ear microcirculation.

CRL 42 339 in an aqueous solution at pH 6.5 (prepared extemporaneously) is administered by gastric route to Half Top rabbit batches (3 males, average weight: 3.5 g; and 3 females, average weight 3.3 kg) under a volume of 2 ml/kg. The very same animals used as control animals against themselves receive distilled water per gastric route, under the very same volume. The following parameters are measured: the terminal arteriole diameter, the terminal veinule diameter, the arteriolar pulsatility, the ear cutaneous temperature, the heart rate and the rectal temperature.

It is found that on awakened Half Top rabbits, CRL 41 339 administered per gastric route moderately dilates for 0.5 h the terminal arteriole, stronghly increases the arteriolar pulsatility and the arteriolar pulsatility/heart rate ratio without modifying the heart rate, induces an important and lasting increase of the ear cutaneous temperature, and exhibits no action on the veinular diameter.

(c) Action on isolated dog vessels.

Annuli of femoral arteriae and external saphenous veins of nembutal-anesthetized dogs are cut off and placed into aerated (O₂: 96%; CO₂: 4%, by volume) Krebs-Henseleit, kept at 37° C. and subjected to a 0.5 g stretching. These vessels are constricted either with noradrenaline $10^{-5}M$ in the presence of propanolol $10^{-6}M$, or with KCl 50 mM in the presence of phentolamine $3 \times 10^{-6}M$. CRL 41 339 is tested at accumulated doses.

It is found that CRL 41 339 exhibits no action on the femoral artery constriction (n=5) and on the external saphenous vein constriction (n=4) induced by KCl in the presence of phentolamine, and that it provokes slakening of the artery (n=5) and of the vein (n=4) constricted by noradrenaline in the presence of propanolol, the molar concentrations (CI-50) which reduce of 50% the contraction being the following ones:
on the artery CI-50=(5.9±3.09)×$10^{-6}M$,
on the vein CI-50=(1.3±0.68)×$10^{-4}M$.

(d) Action on perfused hind quarters of rats.

CRL 41 339 exhibits on nembutal-anesthetized and noradrenaline-constricted hind quarters of rats an important vasodilating effect.

The duration of said effect increases with the dose of CRL 41 339. It is believed that the important anti-noradrenaline activity of CRL 41 339 is involved in the vasodilating activity of said CRL 41 339.

(e) Comparison of salts.

Three dogs anesthetized with nembutal and having an average weight of 12.9 kg are used as control animals vis-a-vis themselves, and are administered per I.A. route in the femoral artery with phenyl-(3-hexamethyleneiminopropyl)-ketone hydrochloride, fumarate and citrate (Ex 1, Code No.: CRL 41 339; Ex 2, Code No.: CRL 41 339A; and respectively Ex 3, code No.: CRL 41 339B), at equimolar doses.

It is found that the injected compound amounts do neither modify the blood pressure nor the heart rate. On the other hand, the three products exhibit an important femoral vasodilating activity as pointed out by the results given in the table II hereinafter and regarding the femoral artery flow (average of 5 assays per product and per dose).

TABLE II

| Product | Code N° | Dose | Femoral flow (ml/min) |
|---|---|---|---|
| Ex 1 (a) | CRL 41 339 | 0 | 64 |
| Ex 1 (a) | CRL 41 339 | $10^{-7}$ M | 83 |
| Ex 1 (a) | CRL 41 339 | $10^{-6}$ M | 117 |
| Ex 1 (a) | CRL 41 339 | $10^{-5}$ M | 166 |
| Ex 2 (b) | CRL 41 339A | 0 | 64 |
| Ex 2 (b) | CRL 41 339A | $10^{-7}$ M | 76 |
| Ex 2 (b) | CRL 41 339A | $10^{-6}$ M | 117 |
| Ex 2 (b) | CRL 41 339A | $10^{-5}$ M | 168 |
| Ex 3 (c) | CRL 41 339B | 0 | 79 |
| Ex 3 (c) | CRL 41 339B | $10^{-7}$ M | 90 |
| Ex 3 (c) | CRL 41 339B | $10^{-6}$ M | 127 |
| Ex 3 (c) | CRL 41 339B | $10^{-5}$ M | 197 |

Notes
(a) phenyl-(3-hexamethyleneiminopropyl)-ketone hydrochloride administered per I.A. route at pH 6;
(b) phenyl-(3-hexamethyleneiminopropyl)-ketone fumarate administered per I.A. route at pH 4;
(c) phenyl-(3-hexamethyleneiminopropyl)-ketone citrate administered per I.A. route at pH 4.

What is claimed is:

1. A phenyl-aminoalkyl-ketone derivative selected from the group consisting of
   (a) the phenyl-(3-hexamethyleneiminopropyl)-ketone of the formula

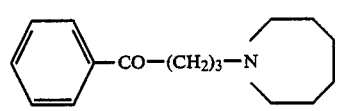

(I)

and,
   (b) its pharmaceutically acceptable addition salts.

2. Phenyl-(3-hexamethyleneiminopropyl)-ketone hydrochloride.

3. A therapeutical composition comprising, in association with a physiologically acceptable excipient, a vasodilating effective amount of phenyl-(3-hexamethyleneiminopropyl)-ketone or one of its non-toxic addition salts according to claim 1.

4. A method of treatment for a patient suffering from circulatory disorders affecting his lower limbs which comprises administering to said patient a vasodilating effective amount of a compound phenyl-(3-hexamethyleneiminopropyl)-ketone of the formula

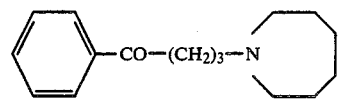

or one of its non-toxic addition salts.

* * * * *